US 6,610,062 B2

(12) United States Patent
Bailey et al.

(10) Patent No.: US 6,610,062 B2
(45) Date of Patent: Aug. 26, 2003

(54) METHOD AND SYSTEM FOR SPINAL FIXATION (75) Inventors: Kirk J. Bailey, Blairstown, NJ (US); Richard P. Dickerson, Rockaway, NJ (US); Gretchen Dougherty Shah, Randolph, NJ (US); Niles L. Noblitt, Mountain Lakes, NJ (US)

(73) Assignee: EBI, L.P., Parsippany, NJ (US)

( * ) Notice: Subject to any disclaimer, the term of this patent is extended or adjusted under 35 U.S.C. 154(b) by 0 days.

(21) Appl. No.: 09/782,713

(22) Filed: Feb. 13, 2001

(65) Prior Publication Data

US 2001/0034521 A1 Oct. 25, 2001

Related U.S. Application Data (60) Provisional application No. 60/182,830, filed on Feb. 16, 2000, and provisional application No. 60/223,061, filed on Aug. 4, 2000.

(51) Int. Cl.⁷ .............................................. A61B 17/70
(52) U.S. Cl. .............................. 606/61; 606/60; 606/73
(58) Field of Search ............................. 606/60, 61, 72, 606/73

(56) References Cited

U.S. PATENT DOCUMENTS

| | | | |
|---|---|---|---|
| 5,176,680 A | 1/1993 | Vignaud et al. | 606/61 |
| 5,486,174 A | 1/1996 | Fournet-Fayard et al. | 606/61 |
| 5,507,746 A | 4/1996 | Lin | 606/61 |
| 5,531,745 A | 7/1996 | Ray | 606/61 |
| 5,569,247 A | 10/1996 | Morrison | 606/61 |
| 5,575,791 A | 11/1996 | Lin | 606/61 |
| 5,702,394 A | 12/1997 | Henry et al. | 606/61 |
| 5,716,357 A | 2/1998 | Rogozinski | 606/61 |
| 5,735,852 A | 4/1998 | Amrein et al. | 606/61 |
| 5,876,403 A | 3/1999 | Shitoto | 606/61 |
| 5,910,142 A | 6/1999 | Tatar | 606/61 |
| 5,938,663 A | 8/1999 | Petreto | 606/61 |
| 5,984,924 A | 11/1999 | Asher et al. | 606/61 |
| 6,004,322 A | 12/1999 | Bernstein | 606/61 |
| 6,010,504 A * | 1/2000 | Rogozinski | 606/61 |
| 6,022,350 A | 2/2000 | Ganem | 606/61 |
| 6,030,388 A | 2/2000 | Yoshimi et al. | 606/61 |
| 6,053,917 A | 4/2000 | Sherman et al. | 606/61 |
| 6,123,706 A * | 9/2000 | Lange | 606/61 |
| 6,299,614 B1 * | 10/2001 | Kretschmer et al. | 606/61 |
| 6,352,537 B1 * | 3/2002 | Strnad | 606/61 |

* cited by examiner

Primary Examiner—Eduardo C. Robert
Assistant Examiner—Michael B. Priddy
(74) Attorney, Agent, or Firm—Harness, Dickey & Pierce, P.L.C.

(57) ABSTRACT

A method and a system for a spinal fixation incorporate a plurality of polydirectional fixation screws and a plurality of linkages. The polydirectional fixation screws include an upper member and a lower member. The upper member is attached to the linkage. The upper member includes a first hemispherical portion. The lower member engages the bone and includes a second hemispherical portion which cooperates with the first hemispherical portion to define a sphere. The second hemispherical portion is coupled to the first hemispherical portion for relative pivotal movement about an axis. Relative movement between the first and second hemispherical portions readily permits sagittal plane adjustments. The polydirectional fixation screw further includes a biasing member for biasing the first member away from the second member in a direction substantially parallel to the axis. The linkages are provided with various vertical offsets to readily permit coronal plane adjustment.

20 Claims, 11 Drawing Sheets

METHOD AND SYSTEM FOR SPINAL FIXATION

CROSS-REFERENCE TO RELATED APPLICATIONS

This application claims priority to provisional applications filed Feb. 16, 2000 (assigned U.S. Ser. No. 60/182,830) and Aug. 4, 2000 (assigned U.S. Ser. No. 60/223,061).

FIELD OF THE INVENTION

The present invention relates generally to the field of spinal fixation devices. More specifically, the present invention is directed to a method and a system for spinal fixation which incorporate a polydirectional fixation screw with a biasing member and vertically offset linkages. The present invention is also directed to a method and system for spinal fixation which incorporates rods and polydirectional couplers.

BACKGROUND OF THE INVENTION

The spinal column is a highly complex structure which houses and protects critical elements of the nervous system. In spite of these complexities, the spinal column is a highly flexible structure, capable of a high degree of curvature and twist through a wide range motion. Genetic or developmental irregularities, trauma, chronic stress, tumors, and disease, however, can result in spinal pathologies which either limit this range of motion, or threaten the critical elements of the nervous system housed within the spinal column.

A variety of systems has been disclosed in the art which achieve immobilization of portions of the spinal column by implanting artificial assemblies in or on the spinal column. These assemblies may be generally classified as anterior, posterior or lateral implants. Posterior implants are attached to the back of the spinal column generally by coupling to the pedicles with screws, or through hooks which attach under the lamina. In either case, the implants generally include elongate support rod elements which are coupled to the screws or hooks to immobilize several sequential vertebrae, for example to hold them stable so that adjacent bones may be fused with bone graft.

Various types of links or plates are also known for spinal fixation.

While known spinal fixation systems have proven to be useful for particular applications, they are all associated with drawbacks. In this regard, the fixation screws or hooks of most known systems are not able to adequately adjust in the sagittal plane or coronal plane. Overcoming this limitation typically requires time consuming reshaping of the rods or plates and links used to connect the hooks or screws. Such bending is a tedious process, which is inconsistent and adds unwanted time to an operation.

The drawbacks discussed above of prior spinal fixation systems are addressed to a significant degree by the SpineLink™ system sold by the assignee of this application. The SpineLink™ system includes a plurality of polydirectional screws which are connected by linkages. Sagittal plane adjustment is achieved through rotation of the polydirectional screw head, thereby substantially eliminating the need for significant contouring of the linkages.

The subject invention further improves upon the SpineLink™ system.

SUMMARY OF THE INVENTION

According to one aspect, the present invention relates to an improved system for spinal fixation which includes a polydirectional fixation screw having a biasing member for normally biasing two partially spherical portions of a head of the screw apart.

According to another aspect, the present invention provides a connection member for adjustably interconnecting a polydirectional screw with a rod.

According to another aspect, the present invention relates to an improved system for spinal fixation which includes a plurality of vertically offset linkages.

According to a more particular aspect, the present invention relates to a connection member for adjustably interconnecting a polydirectional screw with a rod that has an arm radially offset from a longitudinal axis of the screw.

According to another more particular aspect, the present invention relates to a connection member for adjustably interconnecting a polydirectional screw with a rod that incorporates a ball engaging the rod which has a pair of lips or flanges to aid in compression and distraction.

An advantage of the present invention is to provide a system for spinal fixation that allows for adjustment in both the sagittal and coronal planes without the need to bend the connecting linkages.

Another advantage of the present invention is to provide a spinal fixation system including a polydirectional fixation screw having a biasing mechanism for maintaining a desired orientation between cooperating hemispherical portions of the screw during implantation.

In one form, the present invention provides a polydirectional fixation screw for use in connecting a bone with a linkage. The polydirectional fixation screw includes an upper member and a lower member. The upper member is attached to the linkage. The upper member includes a first hemispherical portion. The lower member engages the bone and includes a second hemispherical portion which cooperates with the first hemispherical portion to define a sphere. The second hemispherical portion is coupled to the first hemispherical portion for relative pivotal movement about an axis. The polydirectional fixation screw further includes a biasing member for biasing said first member away from said second member in a direction substantially parallel to the axis.

In another form, the present invention provides a system for spinal fixation. The system includes a rod, a polydirectional fixation screw, a connection member and a nut. The polydirectional fixation screw includes an upper member and a lower member. The upper member has a first hemispherical portion. The lower member includes a second hemispherical portion that cooperates with the first hemispherical portion to substantially define a sphere. The second hemispherical portion is coupled to the first hemispherical portion for relative pivotal movement about an axis. The connection member adjustably interconnects the polydirectional fixation screw and the rod. The connection member includes first and second flanges connected by an intermediate portion. The intermediate portion defines an aperture for receiving the rod. The second flange defines a recess for matingly receiving a portion of the sphere. The nut threadably engages the upper member and is rotatable in a first direction to arrest relative movement between the first and second hemispherical portions and also to arrest relative movement between the rod and the connection member.

BRIEF DESCRIPTION OF THE DRAWINGS

FIG. 7b is a side view of the connection member of FIG. 7a.

FIG. 7c is a top view of the connection member of FIG. 7a.

FIG. 7d is an end view of the connection member of FIG. 7a.

FIG. 8b is a side view of the connection member of FIG. 8a.

FIG. 9b is a side view of the connection member of FIG. 9a.

FIG. 9c is a top view of the connection member of FIG. 9a.

FIG. 9d is an end view of the connection member of FIG. 9a.

DETAILED DESCRIPTION OF THE PREFERRED EMBODIMENTS

The following description of the preferred embodiments of the present invention is merely exemplary in nature and is in no way intended to limit the subject invention or its application or uses.

With general reference to the drawings, a first preferred embodiment of the present invention is directed to a system for spinal fixation 10. As shown particularly in FIGS. 1a and 1b, components of the system have been arranged in an exemplary construct for attachment to a portion of a spinal column 12 of a human patient. The components of the system 10 of the present invention used in the construct generally include a plurality of linkages 14 and a plurality of polydirectional fixation screws 16 for engaging the spinal column 12.

Figure 1B:
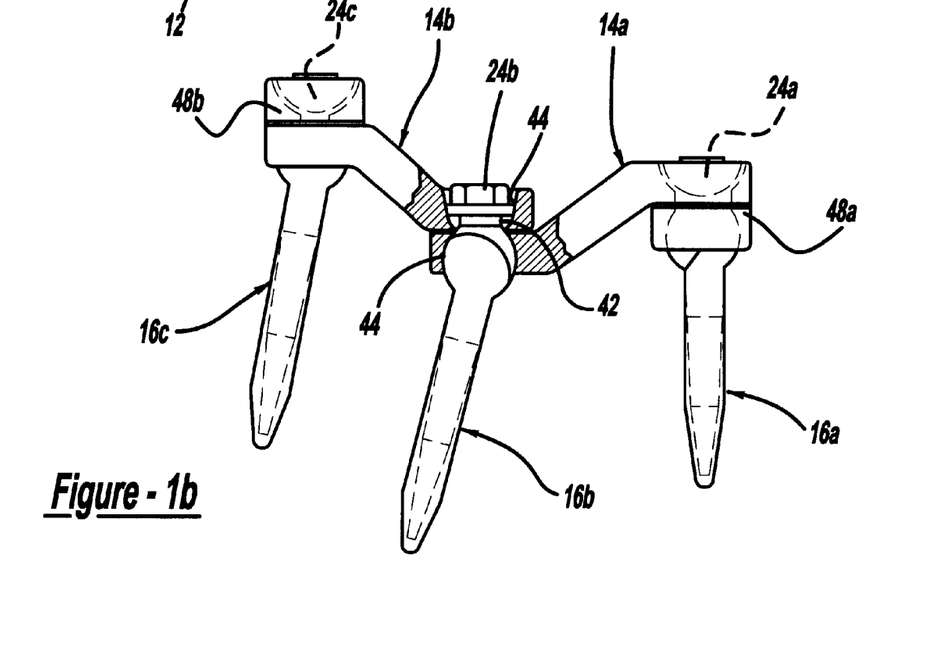
FIG. 1b is a medial-lateral view of a portion of the exemplary construct of FIG. 1a shown partially cut-away.
Figures 2A, 2B:
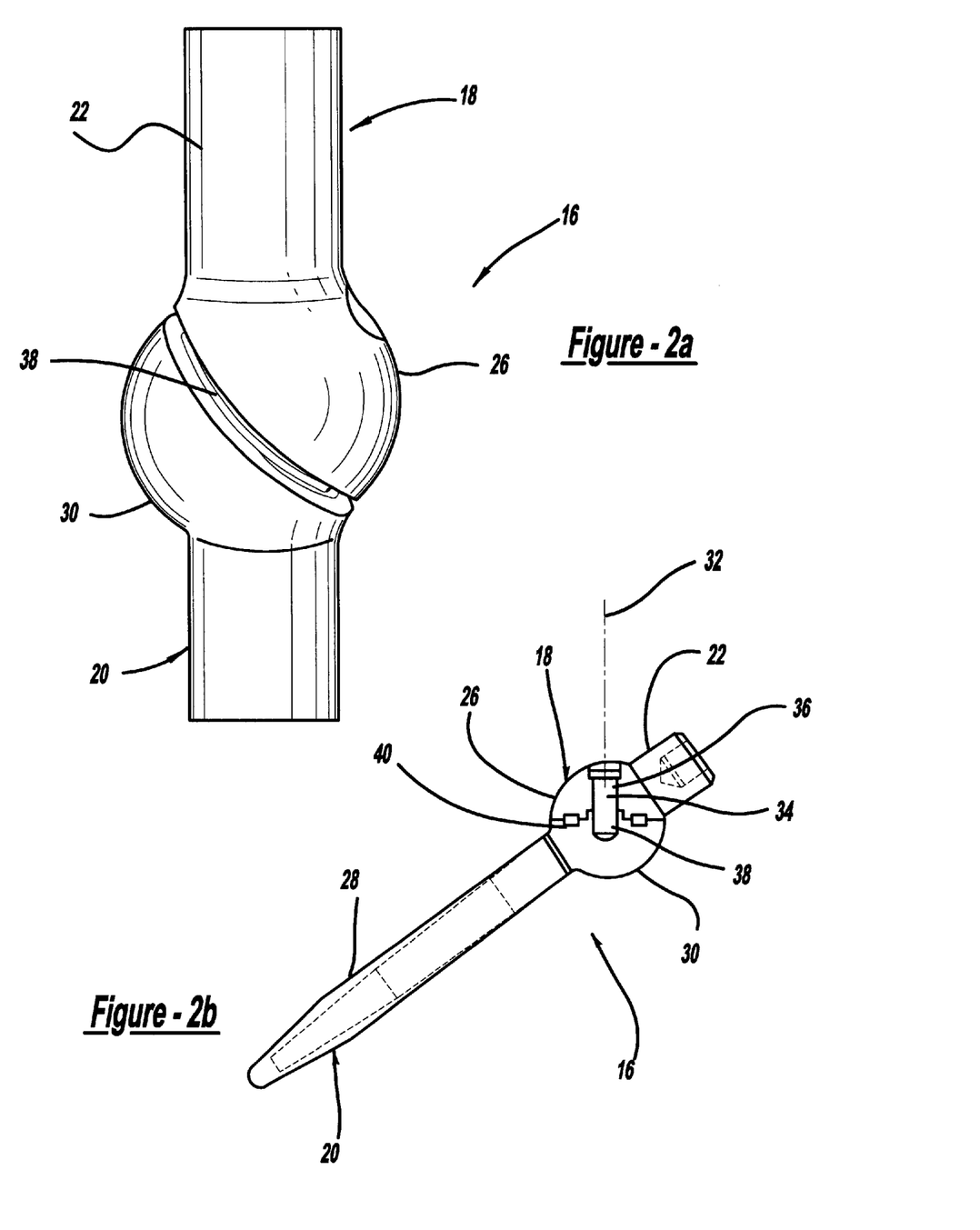
FIGS. 2a and 2b illustrate a polydirectional fixation screw of the system for spinal fixation of the present invention.

With particular reference to FIGS. 2a and 2b, one of the polydirectional fixation screws 16 of the system for spinal fixation 10 of the present invention is illustrated in further detail. The polydirectional fixation screw 16 includes an upper member 18 and a lower member 20. The upper member 18 includes an externally threaded shaft portion or shaft 22 for threadably engaging a nut 24 (shown in FIG. 1b) when the polydirectional fixation screw 16 is secured to a linkage 14 in a manner discussed below. The upper member 18 further includes a first hemispherical portion 26.

The lower member 20 of the polydirectional screw 16 includes an externally threaded shaft or anchor 28 for engaging the spinal column 12 in a conventional manner. The threads of the shaft 28 are shown in the drawings in simplified form. The lower member 20 further includes a second hemispherical portion 30. The second hemispherical portion 30 cooperates with the first hemispherical portion 26 of the upper member 18 to substantially define a complete sphere.

The second hemispherical portion 30 is coupled to the first hemispherical portion 26 for relative pivotal movement about an axis 32. In the embodiment illustrated, a pivot pin 34 passes through an aperture 36 provided in the first hemispherical portion 26 and is press-fit into an aperture 38 provided in the second hemispherical portion 20. The pin 34 defines the axis 32. In the embodiment illustrated, the axis 32 is oriented at an acute angle relative to the upper threaded portion 22. In one application the acute angle is approximately 30 degrees. However, those skilled in the art will readily appreciate that other angles may be employed.

The first hemispherical portion 18 is normally permitted to rotate relative to the second hemispherical portion 20 through 360 degrees about the axis 32. Through this relative motion, sagittal plane adjustment is readily achieved by the surgeon and purchase into the spinal column 12 can be optimized. Explaining further, adjustment of the upper member 18 of the screw 16 relative to the lower member 20 of the screw 16 allows the shaft 28 of the lower member 20 to be inserted into the spinal column 12 at an angle without the need for contouring of the cooperating linkages 14.

In the first preferred embodiment, the polydirectional fixation screw 16 further includes a biasing member 40 for biasing the first hemispherical portion 18 away from the second hemispherical portion 28 in a direction substantially parallel to the axis 32. In the first preferred embodiment, the biasing member is a spring 40 having a generally torodial shape. As shown particularly in FIG. 2b, the biasing member 40 is disposed within cooperating grooves provided in opposed faces of the first and second hemispherical portions 26 and 30. The biasing member 40 defines an aperture through which the axis 32 passes. The biasing member 40 operates to maintain a desired orientation between the upper and lower members 18 and 20 until the first and second hemispherical portions 26 and 30 can be clamped together in the manner discussed below. In certain applications, it may be desirable to put cooperating serrations on adjacent surfaces of the first and second hemispherical portions 26 and 30.

Figure 3A:
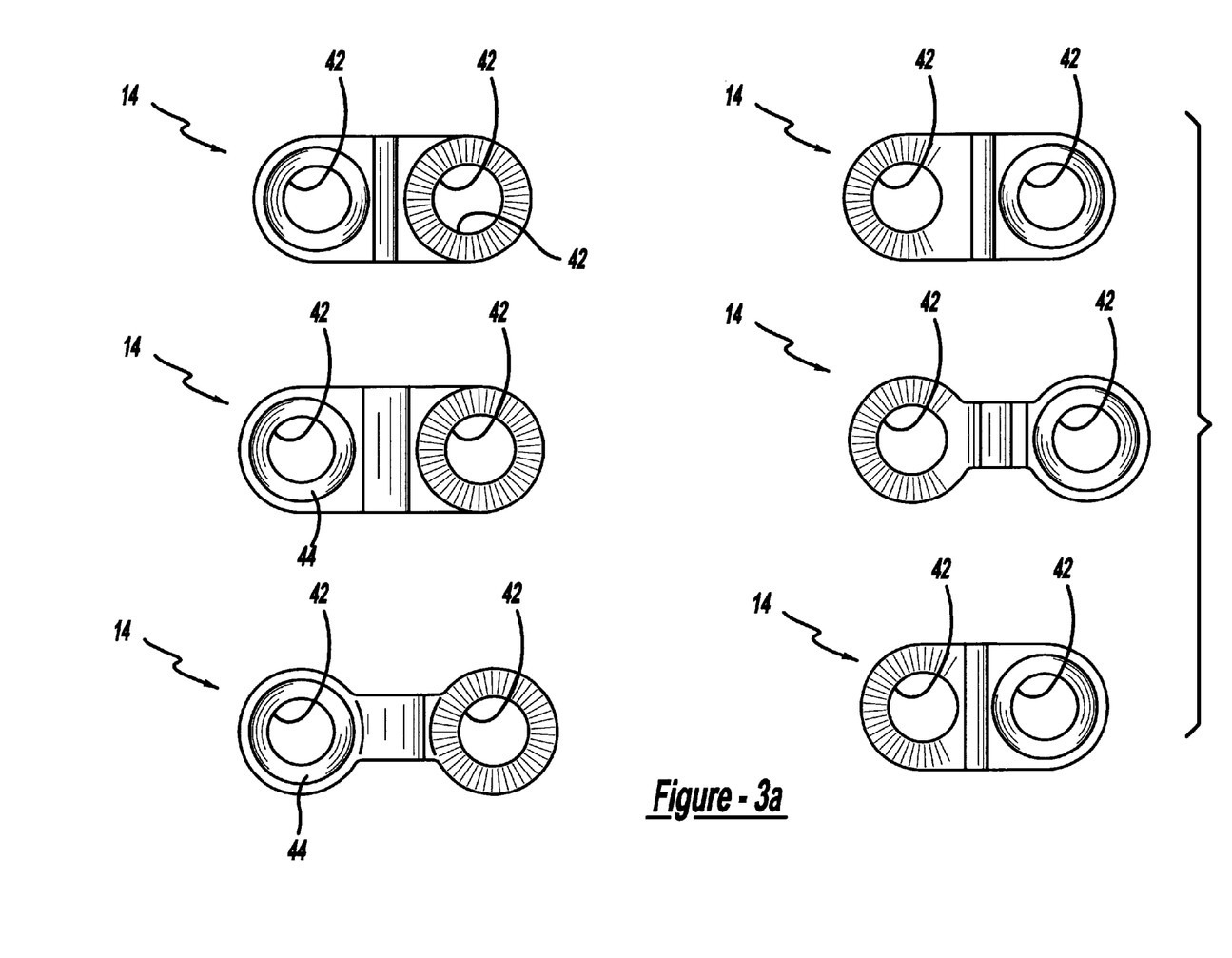
FIGS. 3a and 3b illustrate the linkages of the system for spinal fixation of the first preferred embodiment of the present invention.
Figure 3B:
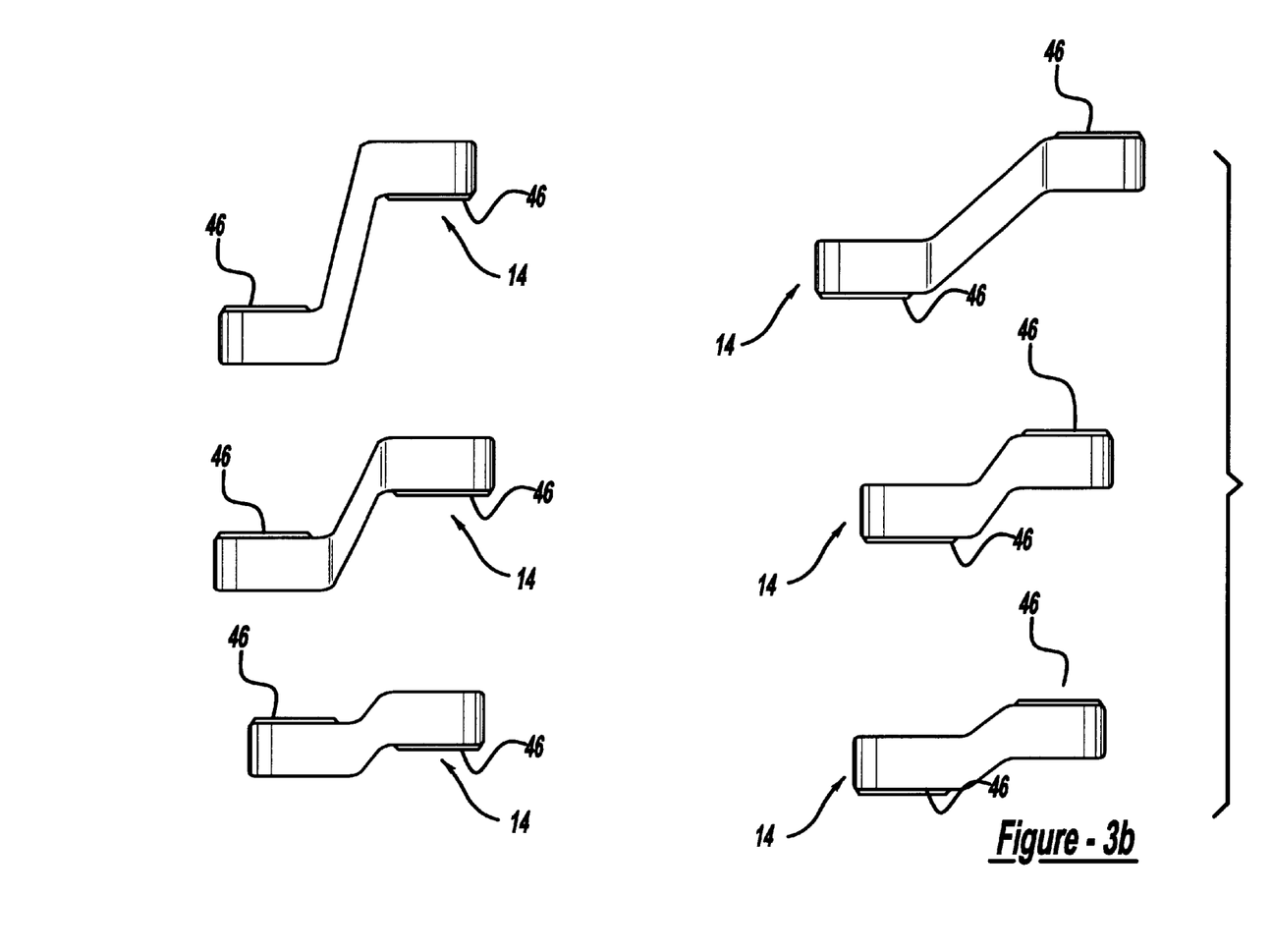

With particular reference to FIGS. 3a and 3b, the linkages 14 of the system for spinal fixation 10 of the present invention are illustrated in further detail. As shown, the linkages 14 are provided in various lengths and vertical offsets to increase the flexibility of the system 10 of the present invention. Such modular linkages 14 permit a surgeon to focus on two points of spinal attachment at a time and address each segment of the spinal column 12 individually. In one application, the linkages 14 of the system 10 are provided with vertical offsets of 3 mm, 6 mm, 9 mm, 12 mm, 15 mm and 18 mm. In this application, the linkages 14 of the system 10 are provided in lengths ranging from approximately 15 mm to approximately 39 mm in increments of 3 mm. It will be understood by those skilled in the art that the degree of vertical offset and the lengths of the linkages is strictly a matter of design choice within the purview of one of ordinary skill in the art.

The linkages 14 are each provided with a pair of apertures 42 located at opposite ends for receiving one of the polydirectional fixation screws 16. The apertures 42 are both associated with substantially identical recesses 44 to matingly receive the spherical shape collectively defined by the first and second hemispherical portions 26 and 30 of the upper and lower member 18 and 20 of the screw 16, respectively. The recesses 44 are also adapted to receive a partially spherical lower surface of one of the nuts 24 (see FIG. 1b). In the exemplary application, the recesses 44 have a conically shaped portion which meets a spherically shaped portion. The recesses 44 at opposite ends of each linkage 14 preferably open in opposite directions.

One side of each end of the linkages 14 is provided with cooperating serrations 46 which radially surround the recesses 44. The serrations 46 cooperate with identical serrations 46 of connected linkages 14 to prevent pivotal movement therebetween. A nut 24 engaging the threaded portion 22 of the upper member 18 serves to clamp the first and second hemispherical portions 26 and 30 together by drawing them against the recess 44 and thereby arrest relative movement between the upper and lower members 18 and 20.

The system 10 of the present invention is further shown to include a plurality of end caps 48. The end caps 48 cooperate with ends of the linkages 14 not coupled to a cooperating linkage 14 for receiving and retaining a screw 16. Each end cap 48 includes an aperture and a recess (shown in phantom in FIG. 1b) similar to corresponding elements of the linkages 14. The end caps 48 also include radially aligned serrations for cooperating with serrations 46 on the adjacent linkage end.

Figure 4A:
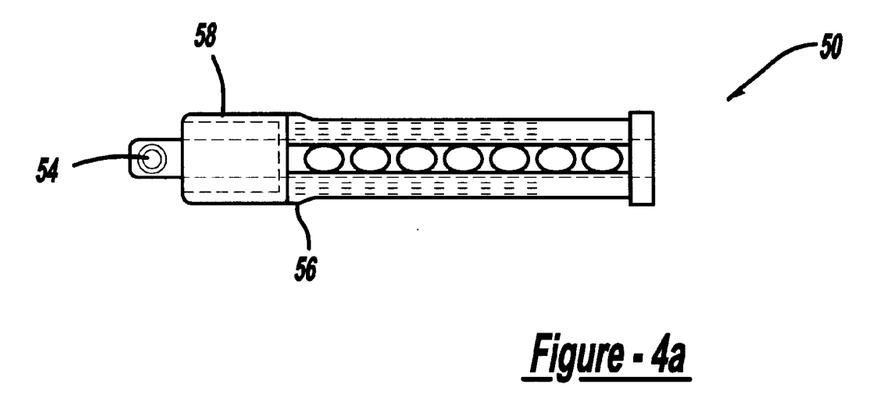
FIGS. 4a and 4b illustrate a caliper for use with the system for spinal fixation of the present invention.
Figure 4B:
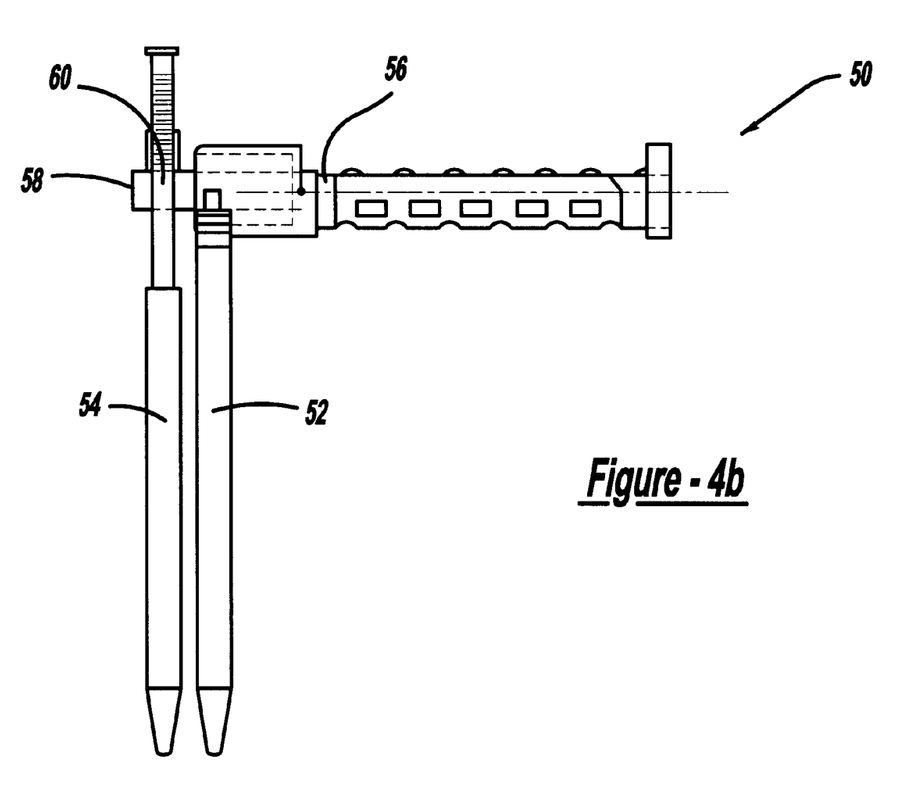

With particular reference to FIGS. 4a and 4b, a caliper 50 for use with the system for spinal fixation 10 of the present invention is illustrated. The caliper 50 includes first and second pointers 52 and 54 for measuring both the horizontal length and vertical height between adjacent spinal portions to be engaged with polydirectional fixation screws 16. The first pointer 52 is secured to a main body 56 of the caliper 50. The second pointer 54 is secured to a linearly translatable arm 58. Graduated markings are provided on the arm 58 and/or the body 56 which indicate the particular horizontal length between the tips of the first and second pointers 52 and 54.

The second pointer 54 is adjustably mounted in an aperture 60 provided in the arm 58 for movement in a direction parallel to the axis defined by the second pointer 54. Graduated markings are provided on the second pointer 54 which indicate the vertical height difference between the tips of the first and second pointers 52 and 54.

Figure 5A:
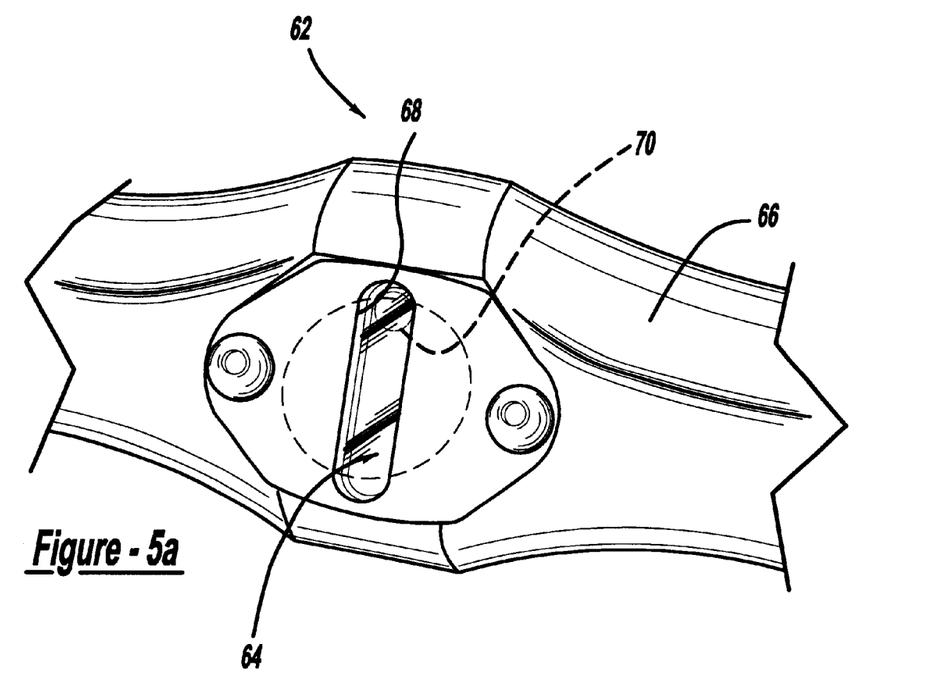
FIGS. 5a and 5b illustrate an insertion tool for use with the system for spinal fixation of the present invention.
Figure 5B:
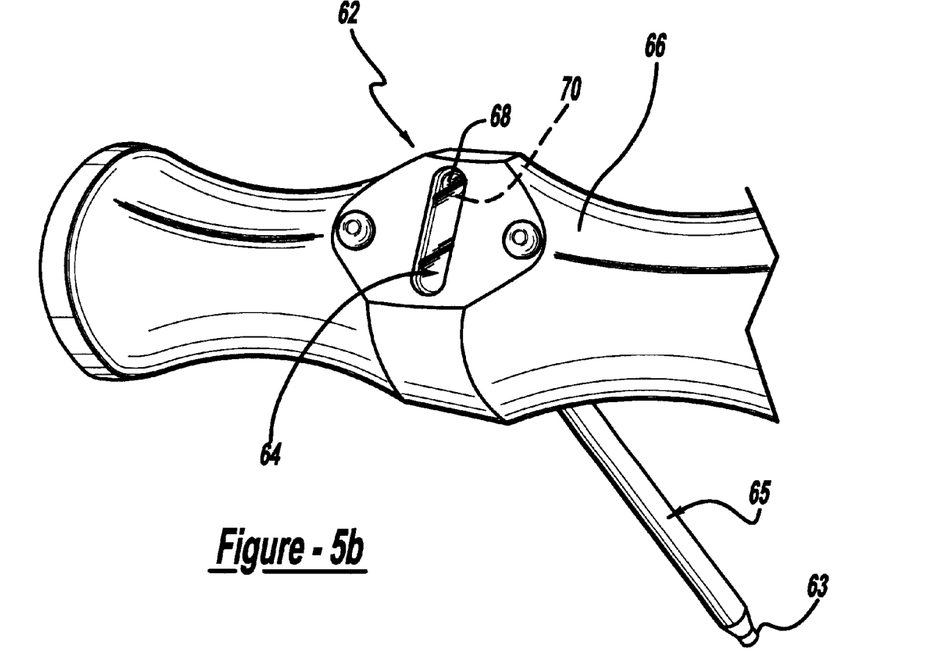

Turning to FIGS. 5a and 5b, an insertion tool 62 for use with the system for spinal fixation 10 of the present invention is illustrated. The insertion tool 62 functions to assist in insertion of the screw 16 so that the upper threaded shaft 22 can be oriented vertically. This orientation has previously been surgically accomplished through trial and error. There are two points in each revolution of the polydirectional fixation screw 16 that the upper threaded shaft 22 can be oriented correctly to a vertical position. A rectangular aperture on the end of the upper threaded shaft 22 is used to drive the screw 16 into the spinal column 12. A rectangular tip 63 at the end of a rod 65 of the insertion tool 62 engages the aperture on the end of the upper threaded shaft 22 such that an upper handle 66 and the pivot axis 32 are in a common plane. A viewing slot 64 is provided on the upper handle 66 which extends in a direction perpendicular to the length of the upper handle 66. A circular bubble level 68 including a bubble 70 is located under the slot 64.

When the screw 16 is turned into the bone, the upper threaded shaft 22 is generally aligned with the lower threaded shaft 20. As the screw 16 is turned, the bubble 70 will appear within the slot 64 twice during a given rotation. When the bubble 70 appears within the slot 64 and the screw is sufficiently set in the bone, the tool 62 can then be used to rotate the upper hemispherical portion 26 relative to the lower hemispherical portion 30. Centering of the bubble 70 within the slot 64 indicates that the upper threaded shaft 22 is vertically aligned.

With reference to FIGS. 6 through 11c, a system for spinal fixation 100 constructed in accordance with the teachings of a second preferred embodiment of the present invention is illustrated. As shown particularly in FIG. 6, components of the system 100 have been arranged in an exemplary construct for attachment to a portion of a spinal column 12 of a human patient in a manner similar to that shown for the system 10 in FIGS. 1a and 1b. The system 100 of the second preferred embodiment of the present invention incorporates polydirectional fasteners or screws 16 identical to those discussed above with respect to the system 10 of the first preferred embodiment. The components of the system 100 used in the exemplary construct further include an elongated linking member preferably in the form of a rod 102, at least one straight connection member or clamp 104 and at least one offset connection member or clamp 106. The connection members 104 and 106 each adjustably interconnect one of a polydirectional fixation screw 16 that engages the spinal column 12 with the rod 102. The intended application of the system 100 is substantially similar as that of the system 10 described above.

With particular reference to FIGS. 7a–7g, the exemplary construct is illustrated to include one straight connection member 104. The connection member 104 is illustrated to generally include a body 108 having a first port ion 110 for engaging the rod 102 and a second portion 112 for engaging the polydirectional fastener 16. The clamp body 108 is shown to have a generally C-shape with an intermediate portion that defines an opening 114 for receiving the rod 102. In the embodiment illustrated, the opening 114 is partially spherical and is adapted to adjustably receive a rod engaging element or spherical locking ball 116.

Figure 10A:
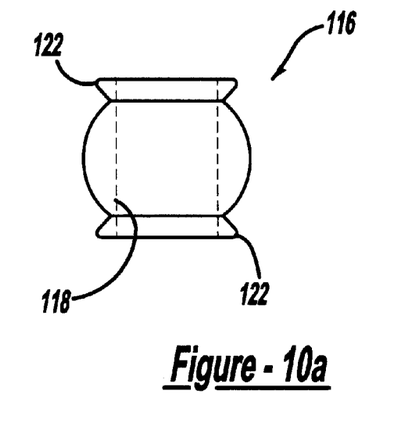
FIGS. 10a and 10b are views of a locking ball of the system of the second preferred embodiment of the present invention.
Figure 10B:
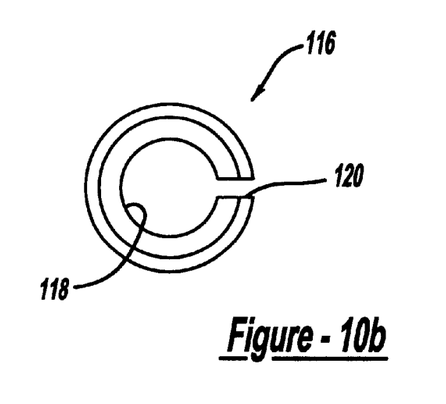

The spherical locking ball 116 is shown particularly in FIGS. 10a and 10b and includes an aperture 118 which passes therethrough for receiving the rod 102. The locking ball 116 is normally permitted to universally move within the opening 114. A slit 120 is provided in the locking ball 116 that engages the aperture 118. Preferably, the locking ball 116 has a pair of lips or flanges 122 that aid in compression and distraction. The flanges 122 extend substantially perpendicular to the direction of the slit 120. Thus, a force applied to the locking ball 116 in a direction parallel to the aperture 118 is received by one of the flanges 122 and does not result in compression of the locking ball 116.

Figure 11A:
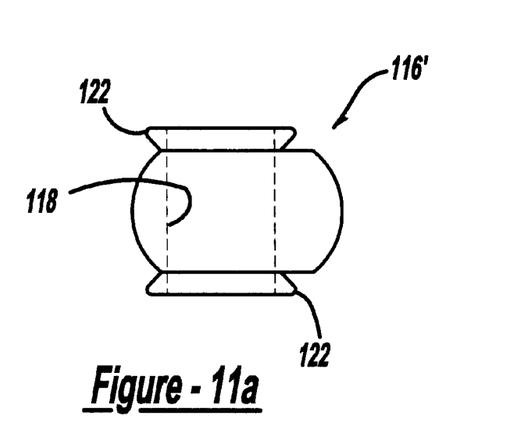
FIGS. 11a through 11c are views of an alternative construction of a locking ball of the system of the second preferred embodiment of the present invention including an eccentric aperture passing therethrough.
Figure 11B:
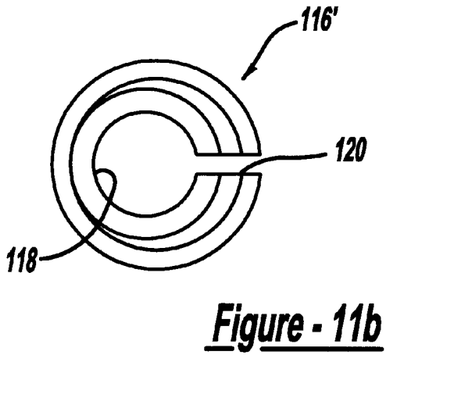
Figure 11C:
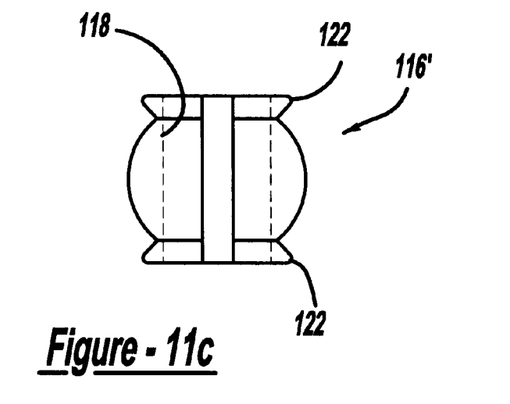

With reference to FIGS. 11a–11c, an alternatively constructed locking ball 116' is illustrated. In this embodiment, the aperture 118 passing through the locking ball 116' is eccentrically located. In one application, the aperture is offset 1 mm from the spherical center of the locking ball 116'. Otherwise, locking balls 116 and 116' are substantially identical.

The clamp body 108 further includes a first or upper flange 124 and a second or lower flange 126. In the embodiment illustrated, the upper and lower flanges 124 and 126 are symmetrical about a plane extending therebetween. The upper and lower flanges 124 and 126 are shown to be generally circular in shape. The intermediate portion or arm of the clamp body 108 between the flanges 124 and 126 extends radially from the upper and lower flanges 124 and 126. The upper and lower flanges 124 and 126 define distinct but aligning apertures 128 and 130, respectively. The apertures 128 and 130 are both associated with substantially identical recesses 132 to mating receive one of the nuts 24 and the spherical shape collectively defined by the first and second hemispherical portions 26 and 30 of the upper and lower member 18 and 20 of the screw 16, respectively. In the exemplary application, the recesses 132 have a conically shaped portion that meets a spherically shaped portion.

As discussed above with respect to the system 10 of the first preferred embodiment, the first hemispherical portion 18 of the polydirectional screw 16 is normally permitted to rotate relative to the second hemispherical portion 20. Through this relative motion, the surgeon readily achieves optimal sagittal plane adjustment and purchase into the spinal column 12. Upon tightening of the nut 24 disposed within the recess 132 of the upper flange 124, movement of the first hemispherical portion 18 relative to the second hemispherical portion 20 is arrested and movement of the clamp body 108 relative to the rod 102 is arrested. Explaining further, tightening of the nut 24 serves to clamp the first and second hemispherical portions 26 and 30 together by drawing them against the recess 132 of the lower flange 126 and thereby arrest relative movement between the upper and lower members 18 and 20. Further tightening of the nut 24 subsequently draws the upper and lower flanges 124 and 126 together causing the intermediate portion of the clamp body 108 to squeeze the locking ball 116 and correspondingly clamp the rod 102.

Importantly, the clamp body 108 is formed to include sufficient spacing between the upper and lower flanges 124 and 126 so that a gap 126 is always maintained throughout the range of tightening. In this manner, clamping forces are more efficiently transferred to the locking ball 116. The clamp body 108 is illustrated in fully clamped condition in FIGS. 7b and 7g.

Figure 8A:
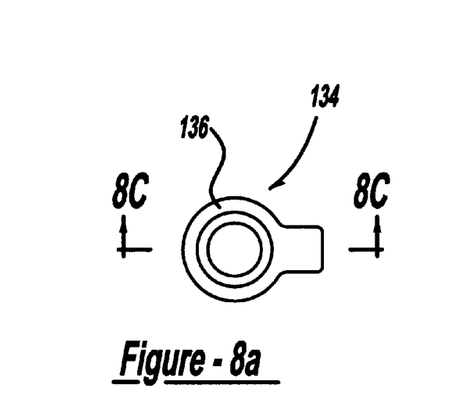
FIG. 8a is a top view of an alternative construction of the connection member with a straight arm of FIGS. 7a–7g.
Figure 8B:
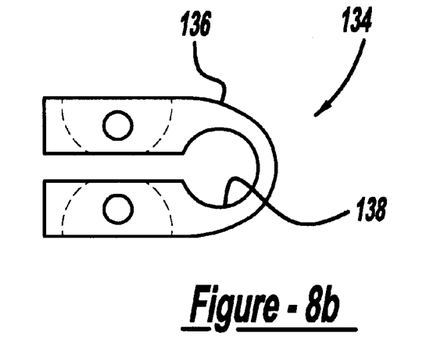
Figure 8C:
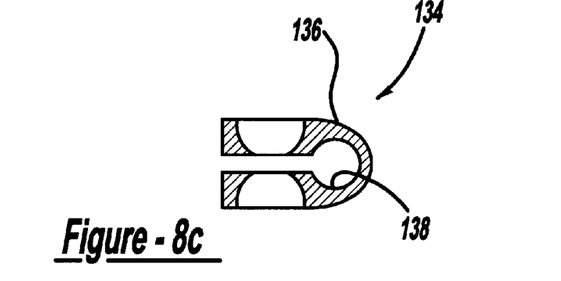
FIG. 8c is a cross-sectional view taken along the line 8c—8c of FIG. 8b.
Figure 9A:
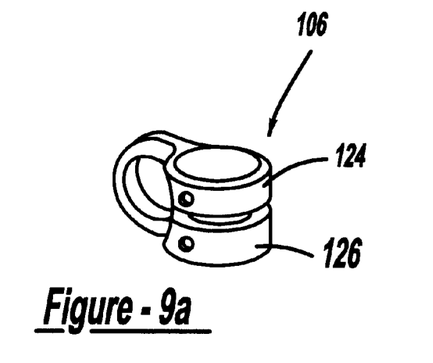
FIG. 9a is a perspective view of a connection member with an offset arm of the system of the second preferred embodiment of the present invention.
Figure 9B:
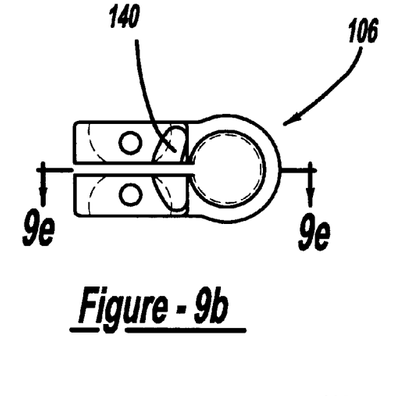
Figure 9C:
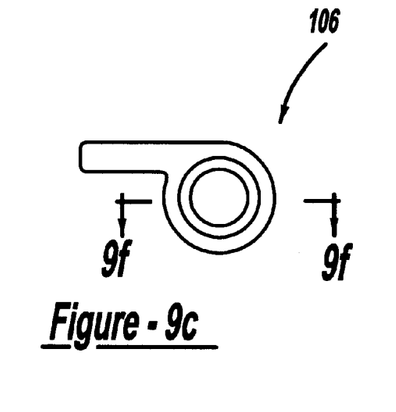
Figure 9D:
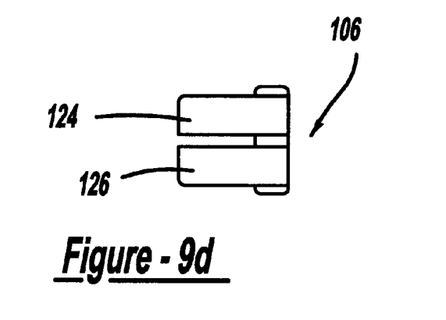
Figure 9E:
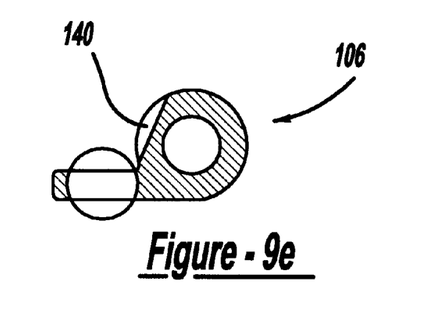
FIG. 9e is a cross-sectional view taken along the line 9e—9e of FIG. 9b.
Figure 9F:
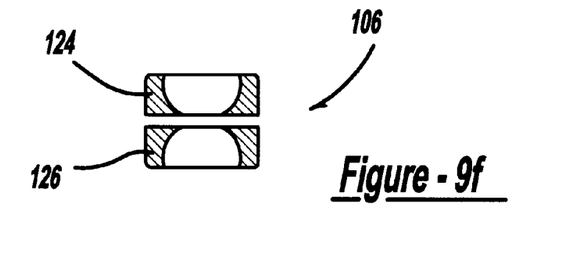
FIG. 9f is a cross-sectional view taken along the line 9f—9f of FIG. 9c.
Figure 9G:
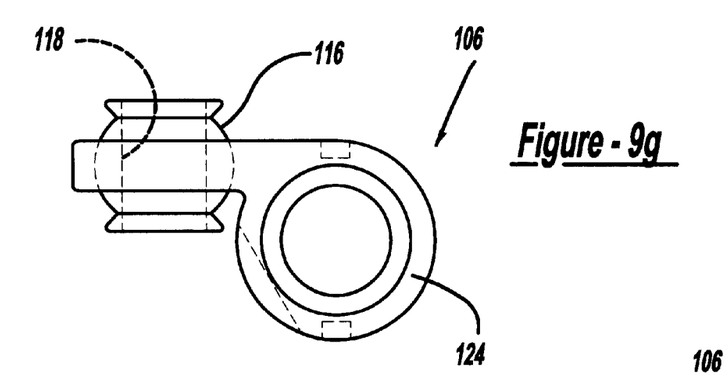
FIG. 9g is a view similar to FIG. 9c, illustrating the connection member operatively associated with a locking ball.
Figure 9H:
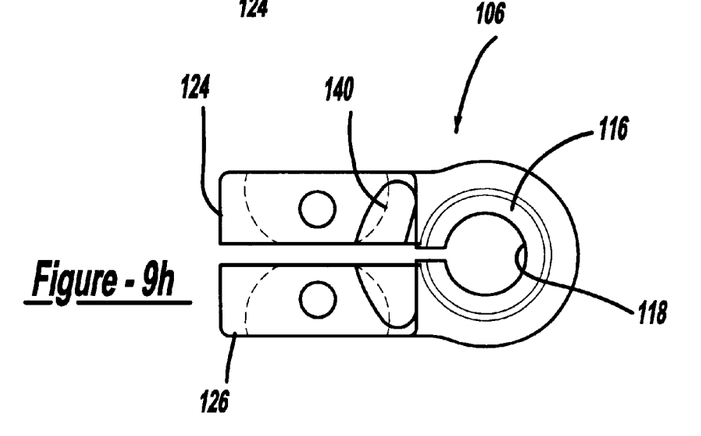
FIG. 9h is a view similar to FIG. 9b, illustrating the connection member operatively associated with a locking ball.

With reference to FIGS. 8a–8c, an alternate construction of the clamp body 108 is illustrated and identified at reference number 134. In this alternative, a clamp body 136 defines a cylindrical aperture 138 for directly receiving the rod 102. Explaining further, the clamp body 134 is not intended to cooperate with a locking ball 116. Otherwise, the clamp body 124 is substantially identical to the clamp body 108.

Figure 6:
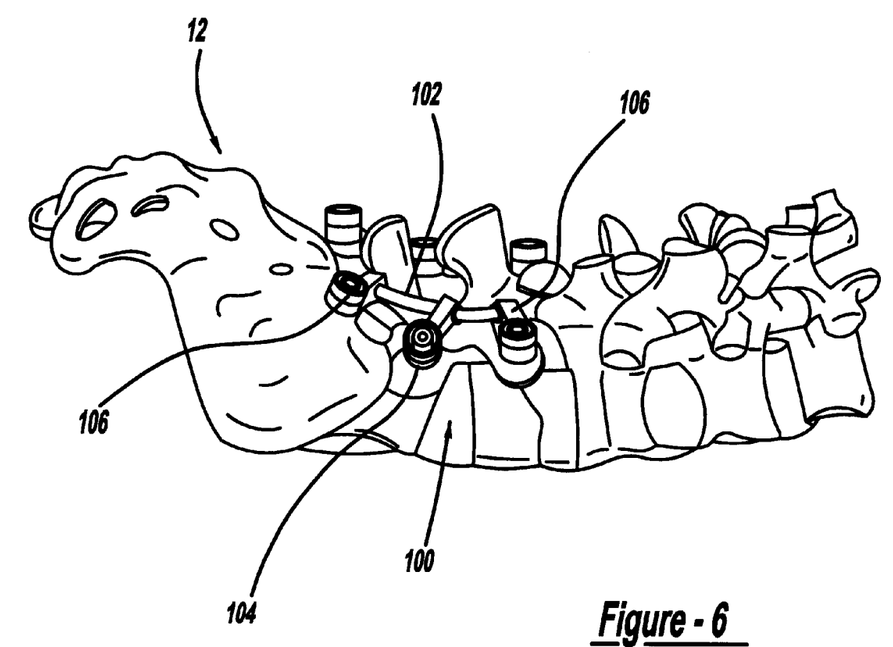
FIG. 6 is a perspective view of a spinal fixation system constructed in accordance with the teachings of a second preferred embodiment of the present invention, the system shown arranged in an exemplary construct and operatively attached to a human spinal column.
Figure 7A:
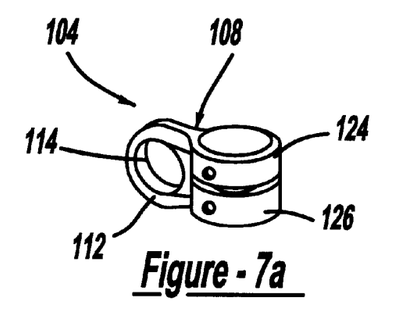
FIG. 7a is a perspective view of a connection member with a straight arm of the system of the second preferred embodiment of the present invention.
Figure 7B:
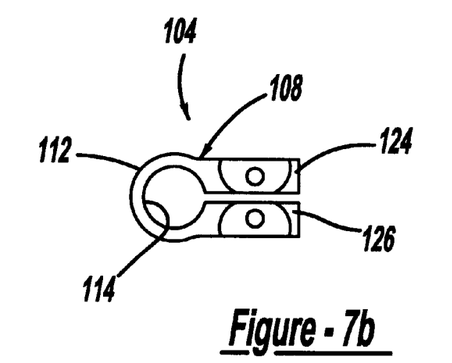
Figure 7C:
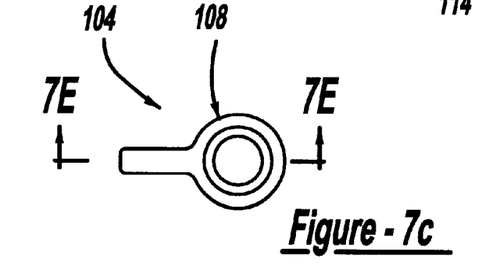
Figure 7D:
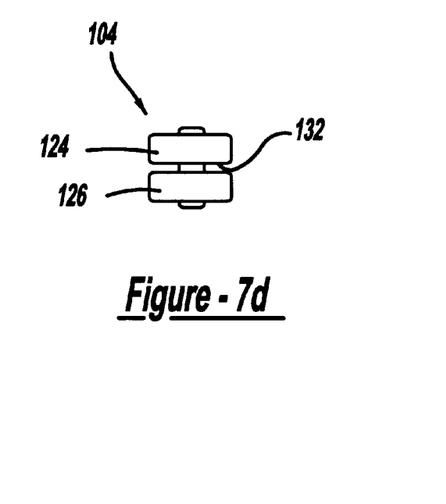
Figure 7E:
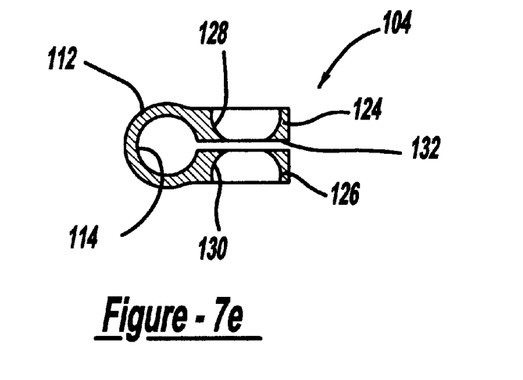
FIG. 7e is a cross-sectional view taken along the line 7e—7e of FIG. 7c.
Figure 7F:
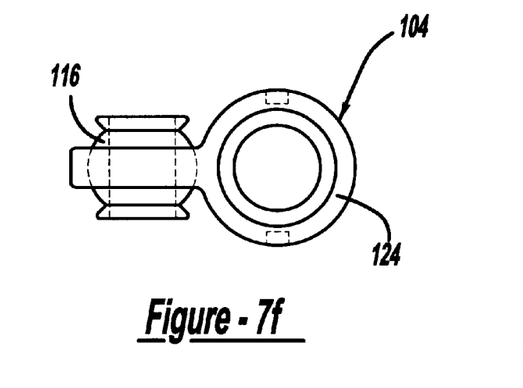
FIG. 7f is a view similar to FIG. 7c, illustrating the connection member operatively associated with a locking ball.
Figure 7G:
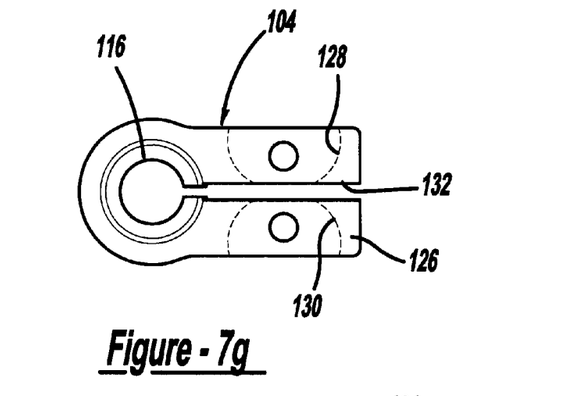
FIG. 7g is a view similar to FIG. 7b, illustrating the connection member operatively associated with a locking ball.

Turning now to FIGS. 9a–9h, the offset arm connection member 106 is further illustrated. The exemplary construct of the system 100 shown in FIG. 6 is illustrated to include a pair of connection members 106. The connection member 106 differs from the connection member 104 primarily in that the intermediate portion or arm is offset to a one side from a radial position. Given this significant degree of similarity between the connection members 104 and 106, like reference numbers have been used in the drawings to identify substantially identical elements. Again, the upper and lower flanges 124 and 126 of the connection member 106 are symmetrical about a plane extending therebetween. This feature allows the surgeon to orient either of the flanges 124 or 126 to receive either of the polydirectional screw 16 and the nut 24. The arm lies in a plane which does not intersect the openings passing through the flanges 124 and 126. The connection member 106 is further shown to include a partially cylindrical relief 140 for receiving a portion of the rod 102 to accommodate a greater range of motion of the rod 102 relative to the connection member 106.

In addition to the various advantages discussed above, the systems 10 and 100 of the present invention do not require the surgeon to start at the lowest point of the construct. Instead, the construct is built from either the most superior or most inferior point on the construct. Therefore, the location of the screws 16 does not affect the ability of the surgeon to build the construct.

According to a method of the present invention, multiple spinal segments are engaged with screws 16. As shown on one side of the spine 12 in FIG. 1a, first, second, and third spinal segments are engaged with first, second and third fixation screws 16a, 16b and 16c, respectively. The second fixation screw 16b engages a spinal segment between the first and third fixation screws 16a and 16c. The spherical portion of the first fixation screw 16a is engaged with a first end cap 48a. The upper threaded shaft 22 of the first fixation screw 16a is engaged with a first nut 24a. The partially spherical lower surface of the first nut 24a received within the first end of a first linkage 14a.

Figure 1A:
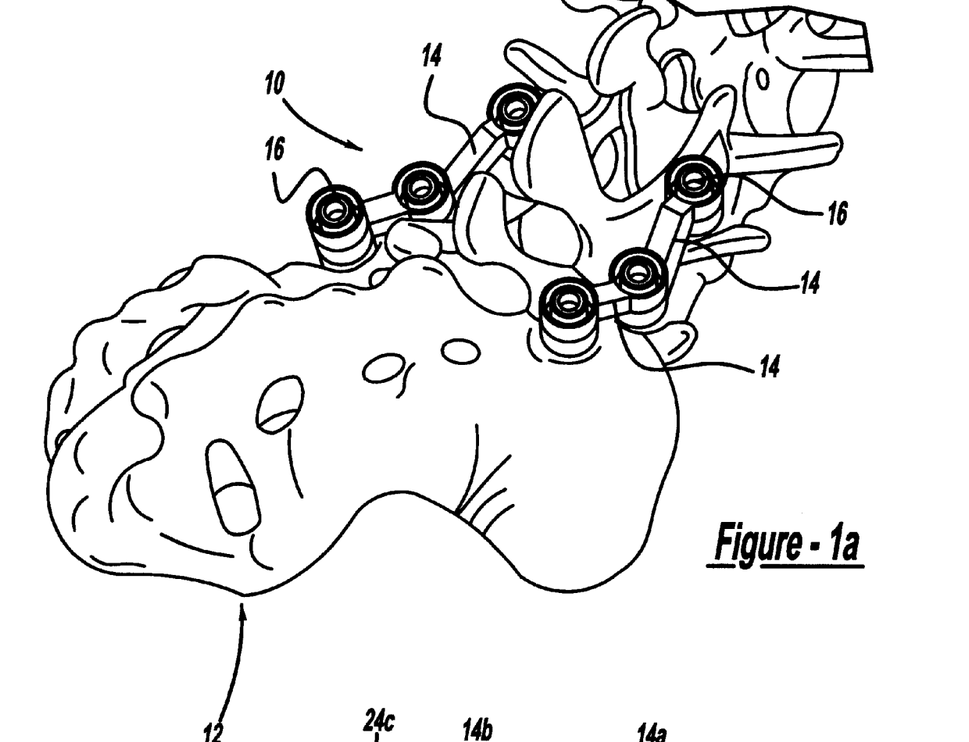
FIG. 1a is a perspective view of a spinal fixation system constructed in accordance with the teachings of a first preferred embodiment of the present invention, the system shown arranged in an exemplary construct and operatively attached to a human spinal column.

Next, a second end of the first linkage 14a is engaged with the spherical portion of the second fixation screw 16b. A second nut 24b is threadably engaged with the second threaded shaft 22 of the second fixation screw 16b. The partially spherical lower surface of the second nut 24b is receiving within a first end of a second linkage 14b.

At this point, the second end of the second linkage 14b is engaged with the spherical portion of the third fixation screw 16c. The second threaded shaft of the third fixation screw 16c is threadably engaged with a third nut 24c. The partially spherical surface of a second end cap 48b receives the partially spherical surface of the third nut 24c.

While the invention has been described in the specification and illustrated in the drawings with reference to preferred embodiments, it will be understood by those skilled in the art that various changes may be made and equivalents may be substituted for elements thereof without departing from the scope of the invention as defined in the claims. In addition, many modifications may be made to adapt a particular situation or material to the teachings of the invention without departing from the essential scope thereof. Therefore, it is intended that the invention not be limited to the particular embodiment illustrated by the drawings and described in the specification as the best mode presently contemplated for carrying out this invention, but that the invention will include any embodiments falling within the description of the appended claims.

What is claimed is:

1. A polydirectional fixation screw for use in connecting a bone with a linkage, the polydirectional fixation screw comprising:
   an upper member for attachment to the linkage, the upper member including a first hemispherical portion;
   a lower member for engagement with the bone, the lower portion including a second hemispherical portion which cooperates with the first hemispherical portion to substantially define a sphere, the second hemispherical portion coupled to the first hemispherical portion for relative pivotal movement about a first axis; and
   a biasing member for biasing said first member away from the second member in a direction substantially parallel to the axis.

2. The polydirectional fixation screw of claim 1, wherein the biasing member is a spring.

3. The polydirectional fixation screw of claim 1, wherein the biasing member defines an aperture, the axis passing through the aperture.

4. The polydirectional fixation screw of claim 1, wherein the upper member includes a threaded portion extending from the first hemispherical portion along a second axis.

5. The polydirectional fixation screw of claim 4, wherein the first axis is disposed at a predetermined angle relative to the second axis.

6. The polydirectional fixation screw of claim 1, wherein the biasing member maintains a desired orientation between the upper and lower members.

7. A system for spinal fixation, the system comprising:
   a rod;
   a polydirectional fixation screw including an upper member and a lower member, the upper member having a first hemispherical portion, the lower member including a second hemispherical portion that cooperates with the first hemispherical portion to substantially define a sphere, the second hemispherical portion coupled to the first hemispherical portion for relative pivotal movement about an axis, the polydirectional screw further including a biasing member for biasing the first member away from the second member in a direction substantially parallel to the axis; and
   a connection member adjustably interconnecting the polydirectional fixation screw and the rod, the connection member including first and second flanges connected by an intermediate portion, the intermediate portion defining an aperture for receiving the rod, the second flange defining a recess for matingly receiving a portion of the sphere; and
   a nut threadably engaging the upper member and rotatable in a first direction to arrest relative movement between the first and second hemispherical portions and to arrest relative movement between the rod and the connection member.

8. The system for spinal fixation of claim 7, wherein the intermediate portion radially extends relative from the first and second flanges.

9. The system for spinal fixation of claim 7, further comprising a locking ball adjustably interconnecting the connection member and the rod, the locking ball defining an aperture receiving the rod.

10. The system for spinal fixation of claim 9, wherein the aperture eccentrically passes through the locking ball.

11. The system for spinal fixation of claim 7, wherein the biasing member defines an aperture, the axis passing through the aperture.

12. A method of spinal fixation comprising the steps of:
   providing a fixation screw having an upper member, a lower member and a biasing member, the upper member for attachment to a linkage and including a first hemispherical portion, the lower member for engagement with the spine and portion including a second hemispherical portion which cooperates with the first hemispherical portion to substantially define a sphere, the second hemispherical portion coupled to the first hemispherical portion for relative pivotal movement about a first axis, the biasing member for biasing said first member away from the second member in a direction substantially parallel to the axis;
   engaging the spine with the lower member;
   orienting the upper member relative to the lower member; and
   maintaining the orientation between the upper and lower members with the biasing member.

13. A spinal fixation system comprising:
   a first fixation screw;
   a second fixation screw; and
   an offset linkage connecting the first fixation screw and the second fixation screw, the offset linkage including a first end engaging the first fixation screw and a second end engaging the second fixation screw, the offset linkage further including an intermediate portion connecting the first and second ends such that a lower surface of the first end is disposed in a first plane and a lower surface of the second end is disposed in a second plane, the first and second planes being parallel and spaced apart.

14. The spinal fixation system of claim 13, wherein the first end has a first opening passing through a first recess, the second end has a second opening passing through a second recess, and the first and second recesses open in opposite directions.

15. The spinal fixation system of claim 13, wherein each of the first and second recesses have a partially spherical configuration.

16. The spinal fixation system of claim 13, wherein both of the first and second fixation screws include an at least partially spherical portion, one of the at least partially spherical portions being matingly received by a recess defined in one of the first and second ends.

17. The spinal fixation system of claim 16, wherein both of the fixation screws further include a threaded upper portion and a nut threadably engaging the upper portion, the nut having an at least partially spherical portion, the at least partially spherical portions of one of the nuts being matingly received by a recess defined in other of the first and second ends.

18. The spinal fixation system of claim 13, wherein both of the first and second fixation screws include an at least partially spherical portion, a threaded upper portion and a nut threadably engaging the upper portion, the nut having an at least partially spherical portion, one of the at least partially spherical portions being matingly received by a recess defined in one of the first and second ends.

19. A coupling for adjustably connecting a rod with a fixation screw, the fixation screw having a spherical portion, a first threaded shaft downwardly extending from the spherical portion, and a second threaded shaft upwardly extending from the spherical portion, the coupling comprising:

an upper generally cylindrical flange having a first opening passing through a first recess, the first recess configured to matingly receive a nut threadably engaging the second threaded shaft;

a lower generally cylindrical flange having a second opening passing through a second recess, the second recess configured to matingly receive the spherical portion of the fixation screw; and an arm connecting the upper and lower flanges, the arm defining an aperture for receiving the rod, the arm disposed in a plane tangential to the upper and lower generally cylindrical flanges.

20. The coupling for adjustably connecting a rod with a fixation screw of claim 19, wherein each of the first and second recesses having a partially spherical configuration.

* * * * *

UNITED STATES PATENT AND TRADEMARK OFFICE
CERTIFICATE OF CORRECTION

PATENT NO. : 6,610,062 B2
DATED : August 26, 2003
INVENTOR(S) : Bailey et al.

It is certified that error appears in the above-identified patent and that said Letters Patent is hereby corrected as shown below:

Title page,
Item [75], Inventors, for "Gretchen Dougherty Shah", "Randolph, NJ" should be -- Wayne, NJ --.
Item [57], ABSTRACT,
Line 2, "incorporate" should be -- incorporates --.

Column 5,
Line 21, delete "address" and substitute -- addresses -- therefor.

Column 7,
Line 1, "por tion" should be -- portion --.

Column 8,
Line 59, delete "receiving" and substitute -- received -- therefor.

Signed and Sealed this

Fourth Day of January, 2005

JON W. DUDAS
*Director of the United States Patent and Trademark Office*